United States Patent [19]

Böhm et al.

[11] Patent Number: 4,880,805

[45] Date of Patent: Nov. 14, 1989

[54] USE OF ALKYLENEDIAMINE DERIVATIVES FOR THE TREATMENT OF BLOOD FLOW DISTURBANCES AND PHARMACEUTICAL COMPOSITIONS CONTAINING THEM

[75] Inventors: Erwin Böhm, Ladenburg; Jens-Peter Hölck, Mannheim; Wolfgang Kampe, Heddesheim; Herbert Leinert, Heppenheim; Bernd Müller-Beckmann, Grünstadt; Klaus Strein, Mannheim, all of Fed. Rep. of Germany

[73] Assignee: Boehringer Mannheim GmbH, Mannheim, Fed. Rep. of Germany

[21] Appl. No.: 222,215

[22] Filed: Jul. 21, 1988

Related U.S. Application Data

[60] Division of Ser. No. 6,275, Jan. 20, 1987, Pat. No. 4,780,474, which is a continuation-in-part of Ser. No. 759,909, Jul. 29, 1985, abandoned.

[30] Foreign Application Priority Data

Aug. 2, 1984 [DE] Fed. Rep. of Germany ....... 3428525

[51] Int. Cl.$^4$ ................ A61K 31/535; A61K 31/415; A61K 31/505; A61K 31/40
[52] U.S. Cl. ............................. 514/237.5; 514/237.8; 514/274; 514/241; 514/242; 514/248; 514/365; 514/374; 514/378; 514/399; 514/354; 514/383; 514/423; 514/432; 514/448; 514/231.8; 514/232.8; 514/233.5; 514/255; 514/418; 514/416; 514/415; 514/419; 514/359
[58] Field of Search ..................... 514/407, 274, 237.5, 514/237.8, 423, 443, 374, 378, 365, 242, 399, 241, 248, 354, 383, 354

[56] References Cited

U.S. PATENT DOCUMENTS

| | | | |
|---|---|---|---|
| 4,172,150 | 10/1979 | Main et al. | 260/553 A |
| 4,356,322 | 10/1982 | Lehmann et al. | 564/185 |
| 4,419,363 | 12/1983 | Smith | 514/403 |
| 4,438,128 | 3/1984 | Wiedermann et al. | 544/277 |
| 4,479,962 | 10/1984 | Wiedermann et al. | 548/371 |

OTHER PUBLICATIONS

Chem. Abst. 73:35038c (1970), Augstein et al.
Chem. Abst. 91:123552t (1979), Lehmann et al.
Chem. Abst. 96:199720v (1982), Wiedemann et al.
Chem. Abst. 99:169058e (1983), Femmer et al.

Primary Examiner—Frederick E. Waddell
Attorney, Agent, or Firm—Felfe & Lynch

[57] ABSTRACT

The present invention is concerned with the use of compounds of the general formula:

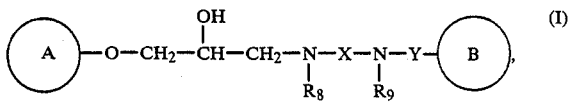

wherein A is an optionally substituted phenyl or heteroaromatic radical, $R_6$ and $R_7$ are hydrogen or lower alkyl, X is an alkylene chain containing up to 6 carbon atoms, Y is a valency bond or a $>C=O$ group and B is an optionally substituted phenyl or heteroaromatic radical, as well as of their pharmacologically acceptable salts for the treatment of blood flow disturbances. The present invention also provides pharmaceutical compositions which contain these compounds.

11 Claims, No Drawings

USE OF ALKYLENEDIAMINE DERIVATIVES FOR THE TREATMENT OF BLOOD FLOW DISTURBANCES AND PHARMACEUTICAL COMPOSITIONS CONTAINING THEM

This application is a divisional of U.S. patent application Ser. No. 006,275 filed Jan. 20, 1987 and now U.S. Pat. No. 4,780,474, which is a continuation-in-part of Ser. No. 759,909, filed July 29, 1985, and now abandoned.

The present invention is concerned with the use of alkylenediamine derivatives for the treatment of blood flow disturbances and with pharmaceutical compositions containing these compounds.

Federal Republic of Germany Patent Specifications Nos. 28 19 629; 28 22 473 (U.S. Pat. No. 4 172 150); 28 44 497 (U.S. Pat. No. 4 356 322); 30 23 369 (U.S. Pat. No. 4 438 128) and 31 31 146 (U.S. Pat. No. 4 479 962) describe alkylenediamines which carry on one nitrogen atom an aryloxypropan-2-ol group and on the other nitrogen atom an aryl or carbamoyl group, these compounds having a more or less marked cardiotonic action.

Thus, for example, 1-phenoxy-3-[2-(1,3,5-trimethyl-pyrazol-4-ylamino)-ethylamino]-propan-2-ol described in Federal Republic of Germany Patent Specification No. 30 23 369 is a compound which acts on $\beta$-receptors and increases the heart-time volume.

Peripheral or cerebral blood flow disturbances cannot be successfully treated solely via these demonstrated effects, i.e. increase of the heart-minute volume, stimulation or blockade of the $\beta$-receptors.

However, a recognised therapy principle for blood flow disturbances is the improvement of the flow properties of the blood, especially the deformability of the erythrocytes.

This is based upon the fact that the erythrocytes, when passing through the capillaries, must be strongly deformed since the erythrocyte diameter is about 7 $\mu$m. whereas the capillary diameter can be as small as 3 $\mu$m.

Patients with peripheral, cerebral or also coronary blood flow disturbances have, as a rule, poorly deformable erythrocytes. In addition, the erythrocytes, in the case of passage through a poorly circulated region, come into contact with metabolic products, such as lactic acid, of which it is known that they further decrease the deformability of the erythrocytes. Finally, the result of this is that erythrocytes regularly can stick in the capillaries and thus obstruct the end flow path for further blood flow.

Surprisingly, we have now found that alkylenediamines disclosed in the above-mentioned Patent Specifications bring about an increase of the deformability of the erythrocytes and, therefore, can be used in therapy of cerebral, coronary and peripheral blood flow disturbances.

Thus, the present invention is concerned with the use of compounds of the general formula:

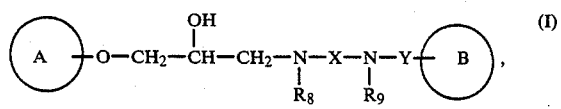

in which (A) is either
1. a phenyl radical of the general formula:

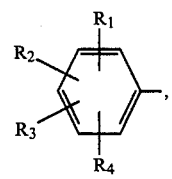

wherein $R_1$, $R_2$, $R_3$ and $R_4$, which are the same or different, are hydrogen, lower alkyl, cyano, carboxamide, halogen, hydroxyl, lower acyloxy, lower alkoxy, methoxy lower alkoxy, lower alkenyloxy, phenyl lower alkoxy, amino or lower acylamino; or
2. a bi- or tricyclic, optionally partly hydrogenated heteroaromatic radical of the general formula:

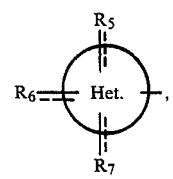

wherein
$R_5$, $R_6$ and $R_7$, which are the same or different, are hydrogen, lower alkyl, benzyl, lower alkanoyl, cyano, hydroxymethyl, lower alkoxycarbonyl, carbamoyl or the divalent residue oxygen or sulphur;
$R_8$ and $R_9$, which are the same or different, are hydrogen or lower alkyl,
X is a straight-chained or branched alkylene chain containing up to 6 carbon atoms,
Y a valency bond or a >C=O group and A is either
1. a phenyl radical of the general formula:

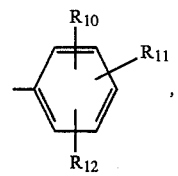

wherein $R_{10}$, $R_{11}$ and $R_{12}$, which are the same or different, are hydrogen, halogen, lower alkyl, lower alkoxy, lower alkylthio, nitro, amino or lower acylamino or $R_{10}$ and $R_{11}$ can together represent an optionally unsaturated trimethylene chain or an alkylenedioxy group; or
2. a mono-, bi- or tricyclic heteroaromatic or hydroheteroaromatic radical of the general formula:

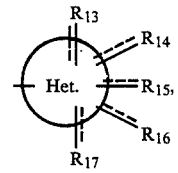

wherein $R_{13}$, $R_{14}$, $R_{15}$, $R_{16}$ and $R_{17}$, which are the same or different, are mono- or divalent substituents selected from hydrogen, halogen, lower alkyl, allyl, lower alkoxy, allyloxy, nitro, amino, lower acylamino, cyano, phenyl lower alkyl, optionally substituted phenyl, oxygen and sulphur; or 3. an amine radical of the general formula:

wherein $R_{18}$ and $R_{19}$, which are the same or different, are hydrogen, lower alkyl, hydroxy lower alkyl, alkoxy lower alkyl or phenyl or, together with the nitrogen atom, form a ring optionally interrupted by at least one heteroatom, such as oxygen, sulphur or the group $>N—R_{20}$, $R_{20}$ being lower alkyl, optionally substituted phenyl, lower alkanoyl or optionally substituted benzoyl, and their pharmacologically acceptable salts for the treatment of blood flow disturbances, as well as pharmaceutical compositions which contain these compounds.

In all cases, lower alkyl means a radical with 1 to 6 and preferably 1 to 4 carbon atoms, especially methyl and ethyl.

In all cases, lower alkoxy as such or in compound radicals means a radical with 1 to 6 and preferably 1 to 4 carbon atoms, especially methoxy and ethoxy.

Lower alkylthio means a $C_1$ to $C_6$-alkylthio radical, especially methylthio.

Lower acyl as such or in compound radicals means a $C_1$ to $C_6$-acyl radical, such as formyl, acetyl, propionyl and butyryl.

Lower alkenyloxy preferably means allyloxy.

An alkylenedioxy radical, which $R_{10}$ and $R_{11}$ can form together, is preferably a $—O—CH_2—O—$ radical.

Aryl and aroyl radicals can carry conventional substituents, such as halogen, hydroxyl, lower alkyl, lower alkoxy, nitro or amino.

Cyclic groups which, according to general formula VI, can be formed by the nitrogen and the radicals $R_{18}$ and $R_{19}$, are preferably piperidine, optionally substituted piperazine and morpholine.

Halogen means fluorine, chlorine, bromine and iodine, especially fluorine and chlorine.

Bi- or tricyclic heteroaromatic radicals A are, for example, indole, indolizine, isoindole, benztriazole, indazole, purine, quinolizine, isoquinoline, quinoline, quinoxaline, quinazoline, cinnoline, carboline, carbazole, acridine, benzthiadiazole, phenazine or benzimidazole and are preferably indole, benzimidazole, indazole, benztriazole or carbazole or partly hydrogenated heteroaromatic radicals, for example indoline, isoindoline, pyrroline or imidazoline and preferably indoline.

Mono-, bi- or tricyclic heteroaromatic radicals B are, for example, the following heteroaromatic radicals: pyrrole, thiophene, oxazole, isoxazole, thiazole, pyrazole, imidazole, 1,2,4-triazole, pyridine, pyrimidine, pyridazine, pyrazine, 1,2,4-triazine, 1,3,5-triazine, thionaphthene, indole, isoindole, benzoxazole, benzthiazole, 1,2-benzisothiazole, benzimidazole, indazole, benztriazole, quinoline, isoquinoline, quinazoline, cinnoline, quinoxaline, phthalazine, carbazole, β-carboline, pyrazolo[3,4-b]pyridine, pyrazolo[3,4-d]pyrimidine and purine, as well as corresponding hydroheteroaromatic radicals derived therefrom, whereby the linkage with the

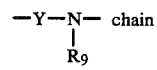

can take place on a ring carbon atom or also on a ring nitrogen atom of the heterocycles concerned.

Hydroheteroaromatic radicals A in the meaning of the present invention are partly hydrogenated derivatives of bi- and tricyclic heterocycles, for example, indoline, 1,2,3,4-tetrahydrocarbazole and non or completely hydrogenated monocyclic heterocycles, such as pyrrolidine and piperidine.

The chain X is preferably an ethylene or propylene chain.

Preferred compounds of general formula (I) used according to the present invention include compounds in which A is a phenyl radical, which is optionally substituted by hydroxyl, or an indazole, indole, benzimidazole or benztriazole radical, $R_8$ and $R_9$ are hydrogen or methyl, X is ethylene, Y is a valency bond or a $>CO$ group and B is a phenyl radical, which is optionally substituted by methyl radicals, a pyrazole radical, which can be substituted one to three times by methyl, propyl or allyl, or a pyrimidine-2,4-dione radical, which can be substituted one to three times by methyl.

In particular, the following compounds are preferred:
(a) 1-phenoxy-3-[2-(1,3,5-trimethylpyrazol-4-ylamino)ethylamino]-propan-2-ol
(b) 1-(4-hydroxyphenoxy)-3-[2-(morpholinocarbonamido)ethylamino]-propan-2-ol
(c) 1-phenoxy-3-[2-(1,3,5-trimethylpyrimidine-2,4-dione-6-yl-N-methylamino)-ethylamino]-propan-2-ol
(d) 1-phenoxy-3-[2-(1-allyl-3,5-dimethylpyrazol-4-ylamino)-ethylamino]-propan-2-ol
(e) 1-phenoxy-3-[2-(1-n-propyl-3,5-dimethylpyrazol-4-ylamino)-ethylamino]-propan-2-ol
(f) 1-(4-hydroxyphenoxy)-3-[2-(1,3,5-trimethylpyrazol-4-ylamino)-ethylamino]-propan-2-ol
(g) 1-phenoxy-3-[2-(1,4-dimethylpyrazol-5-ylamino)ethylamino]-propan-2-ol
(h) 1-(indazol-4-yloxy)-3-[2-(2,6-dimethylphenylamino)ethylamino]-propan-2-ol.

Some of the compounds used according to the present invention are new. They can be prepared by the processes described in the above-mentioned Patent Specifications.

For the preparation of pharmaceutical compositions, compounds of general formula (I) are mixed in known manner with appropriate pharmaceutical carriers, aroma, flavouring and colouring materials and formed, for example, into tablets or dragees or, with the addition of appropriate adjuvants, are suspended or dissolved in water or an oil, for example olive oil.

The compounds of general formula (I) used according to the present invention and their salts can be administered enterally or parenterally in liquid or solid form. As injection medium, water is preferably used which contains the additives usual in the case of injection solutions, such as stabilising agents, solubilising agents or buffers. Such additives include, for example, tartrate and citrate buffers, ethanol, complex formers (such as ethylenediamine-tetraacetic acid and its non-toxic salts) and high molecular weight polymers (such as liquid polyethylene oxide) for viscosity regulation. Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavouring and sweetening materials.

The dose to be used in the case of humans depends upon the age, weight and general condition of the patient, the severity of the disease, the nature of other simultaneous treatments, the frequency of administration and the nature of the intended action. The daily dosage of the active compound is usually 0.1 to 50 mg. per/kg. of body weight. Normally, 0.5 to 40 mg. and preferably 1.0 to 20 mg./kg./day in one or more single doses should suffice in order to achieve the desired improvement.

The deformability of the erythrocytes is usually measured in the so-called filtration test. A suspension of erythrocytes is thereby passed through a filter which has pores with a diameter which corresponds to that of small capillaries. A compound which improves the deformability of the erythrocytes must also simultaneously increase the passage of the erythrocytes through these filter pores and thus the filterability of the erythrocyte suspension.

In the present case, we have investigated to what extent the addition of the compounds used according to the present invention to a suspension of human erythrocytes changes their deformability. The human erythrocytes originated from patients with peripheral and cerebral blood flow disturbances which were more poorly deformable than erythrocytes of healthy subjects.

The following compounds were investigated:
(a) 1-phenoxy-3-[2-(1,3,5-trimethylpyrazol-4-ylamino)ethylamino]-propan-2-ol
(b) 1-(4-hydroxyphenoxy)-3-[2-(morpholinecarbonamido)ethylamino]-propan-2-ol
(c) 1-phenoxy-3-[2-(1,3,5-trimethylpyrimidine-2,4-dion-6-yl-N-methylamino)-ethylamino]-propan-2-ol
(d) 1-phenoxy-3-[2-(1-allyl-3,5-dimethylpyrazol-4-ylamino)-ethylamino]-propan-2-ol
(e) 1-phenoxy-3-[2-(1-n-propyl-3,5-dimethylpyrazol-4-ylamino)-ethylamino]-propan-2-ol
(f) 1-(4-hydroxyphenoxy)-3-[2-(1,3,5-trimethylpyrazol-4-ylamino)-ethylamino]-propan-2-ol
(g) 1-phenoxy-3-[2-(1,4-dimethylpyrazol-5-ylamino)ethylamino]-propan-2-ol.

As comparison substance, there was chosen the commercially available pentoxifylline (Trental) (3,7-dihydro-3,7-dimethyl-1-(5-oxohexyl)-1H-purine-2,6-dione).

DESCRIPTION OF METHODS

Determination of erythrocyte filterability

A. Method according to Dodds and Dormandy[1]

Blood with pathological-rheological properties (deformation index less than 0.55) was worked up and filtered as follows: The blood anticoagulated with lithium heparin was centrifuged for 15 minutes at 3000 r.p.m. The plasma was first prefiltered through filters with a pore size of 1.2 $\mu$m. in order to retain protein precipitates. After removal of the buffy coat, the erythrocytes were resuspended in autologous plasma so that a haemocrit of 5% resulted. 1 ml. amounts thereof were subsequently allowed to run through a nucleopore filter with a pore size of 5 $\mu$m. The filtration was discontinued after 60 seconds. Subsequently, the deformation index was determined, i.e. the ratio between the optical density of the filtrate and that of the unfiltered suspension. Correspondingly, all values lie between 0 and 1. In the case of healthy donors, the index so obtained is 0.63 (standard deviation 0.2).

B. Filtration with the SER method[2] (=selective erythrocyte rigidometer).

Blood was taken from patients with peripheral blood flow disturbances (stage II according to Fontaine) and mixed with sodium heparinate. The blood was centrifuged and the plasmas fractionated into several equally large portions. To each fraction was added a different compound or a compound in different concentrations.

After the addition of the test compounds, the blood cells were resuspended and a haemocrit value of 45% adjusted. All blood samples were incubated for 60 minutes at 37° C. In order to ensure a pH constancy at 7.4, during the incubation time the samples were covered with Carbogen (80% oxygen and 20% carbon dioxide). Subsequently, the passage time of 250 erythrocytes was determined with the help of the SER apparatus, the single pore thereof having a definite diameter and a definite length. The driving pressure is so chosen that the resulting shearing stress remains within the physiological range. As a comparative value, the average erythrocyte passage time of all 250 erythrocytes is determined in milliseconds.

The results obtained are summarised in the following Table:

TABLE

Summary of haemorheological findings
D + D = method according to Dodds and Dormandy[1];
measurement value = deformation index (larger values correspond to a better erythrocyte deformability).
SER = selective erythrocyte rigidometer[2];
measurement value = average passage time in msec.
(smaller values correspond to better erythrocyte deformability)

| substance | conc. (mol/l) | method | total No. of patients | average value | rheolog. improvement result thereof | average value |
|---|---|---|---|---|---|---|
|     | $10^{-8}$ | D + D | 10 | 0.48 | 4 | 0.48 |
| (a) | $10^{-8}$ | D + D | 10 | 0.48 | 8 | 0.56 |
|     | $10^{-9}$ | D + D | 10 | 0.48 | 10 | 0.57 |
|     | $10^{-6}$ | SER | 10 | 20.24 | 7 | 19.48 |
|     | $10^{-7}$ | SER | 10 | 20.24 | 9 | 18.68 |
|     | $10^{-8}$ | SER | 10 | 20.24 | 9 | 19.02 |

TABLE-continued

Summary of haemorheological findings
D + D = method according to Dodds and Dormandy[1];
measurement value = deformation index (larger values correspond to a better erythrocyte deformability).
SER = selective erythrocyte rigidometer[2];
measurement value = average passage time in msec.
(smaller values correspond to better erythrocyte deformability)

| substance | conc. (mol/l) | method | total No. of patients | average value | rheolog. improvement result thereof | average value |
|---|---|---|---|---|---|---|
|  | $10^{-6}$ | D + D | 6 | 0.48 | 3 | 0.50 |
| (b) | $10^{-8}$ | D + D | 6 | 0.48 | 5 | 0.52 |
| (c) | $10^{-8}$ | SER | 3 | 17.97 | 2 | 17.20 |
| (d) | $10^{-8}$ | SER | 3 | 17.97 | 2 | 16.57 |
| (e) | $10^{-8}$ | SER | 3 | 17.97 | 3 | 16.93 |
| (f) | $10^{-8}$ | SER | 3 | 17.97 | 1 | 17.90 |
| (g) | $10^{-8}$ | SER | 3 | 17.97 | 1 | 18.13 |
| pentoxifylline | $0.9 \times 10^{-5}$ | D + D | 10 | 0.48 | 5 | 0.49 |
| (comparison substance) | $0.9 \times 10^{-5}$ | D + D | 6 | 0.48 | 4 | 0.51 |
|  | $1.8 \times 10^{-5}$ | SER | 10 | 20.24 | 10 | 18.13 |

Results

The results given in the above Table show that the tested compounds result in an improvement of the erythrocyte deformability. For the compound (a) and pentoxifylline, this effect could even be ascertained with two different methods.

These effects show that the investigated compounds are suitable for the treatment of peripheral and cerebral blood flow disturbances and of other diseases which accompany changes of the flow properties.

Literature references (1) Dodds, A. J.; M. J. G. O'Reilly; C. J. P. Yates; L. T. Cotton; P. T. Fluite; J. A. Dormandy: Haemorrheological response to plasma exchange in Raynaud's syndrome, B. M. J., 2, 1186–1187/1979.

(2) Roggenkamp, H. G.; F. Jung; H. Kiesewetter: An apparatus for the electrical measurement of the deformability of erythrocytes, Biomed. Tech., 28, 100–104/1983.

It will be understood that the specification and examples are illustrative but not limitative of the present invention and that other embodiments within the spirit and scope of the invention will suggest themselves to those skilled in the art.

What is claimed is:

1. Method for treating a blood flow disturbance characterized by reduced deformability of erythrocytes comprising administering to a subject with such a blood flow disturbance, in an amount effective to increase the deformability of erythrocytes in the blood an alkylenediamine of the formula:

$$A-O-CH_2-\underset{OH}{\underset{|}{CH}}-CH_2-\underset{R_8}{\underset{|}{N}}-X-\underset{R_9}{\underset{|}{N}}-Y-B$$

wherein A is a phenyl radical of the formula

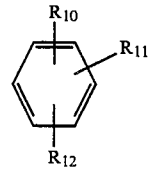

wherein $R_{10}$, $R_{11}$ and $R_{12}$, are individually selected from the group consisting of hydrogen, halogen, lower alkyl of 1 to 6 carbon atoms, lower alkoxy of 1 to 6 carbon atoms, lower alkylthio of 1 to 6 carbon atoms, nitro, amino and lower acylamine of 1 to 6 carbon atoms or $R_{10}$ and $R_{11}$ can together represent a saturated or unsaturated trimethylene chain or an alkylenedioxy group of 1 to 6 carbon atoms and B is a mono-, di- or tricyclic heteroaromatic or hydroheteroaromatic of the formula:

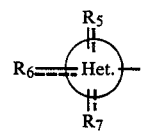

wherein
  $R_5$, $R_6$ and $R_7$, are individually selected from the group consisting of hydrogen, lower alkyl of 1 to 6 carbon atoms, benzyl, lower alkanoyl of 1 to 6 carbon atoms, cyano, hydroxymethyl, lower alkoxycarbonyl wherein the alkoxy contains 1 to 6 carbon atoms, carbamoyl and divalent oxygen or sulphur, $R_8$ is hydrogen or lower alkyl of 1 to 6 carbon atoms, and $R_9$ is hydrogen or lower alkyl of 1 to 6 carbon atoms,
  X is straight-chained or branched alkylene chain containing up to 6 carbon atoms,
  Y is a valency bond or a C=O group and their pharmacologically acceptable salts.

2. The method of claim 1, wherein A is phenyl or phenyl substituted 1 to 3 times by hydroxyl, $R_8$ and $R_9$ are hydrogen or methyl,
  X is ethylene, Y is a valency bond or a >CO group, and B is pyrazole, pyrazole substituted one to three times by methyl, propyl or allyl; pyrimidine-2,4-dione; or pyrimidine-2,4-dione substituted one to three times by methyl.

3. The method of claim 1 wherein 1-phenoxy-3[2-(1,3,5-trimethylpyrazol-4-ylamino)-ethylamino]-propan-2-ol is administered.

4. The method of claim 1 wherein 1-(4-hydroxyphenoxy)-3-[2-(morpholinocarbonamido)-ethylamino]-propan-2-ol is administered.

5. The method of claim 1 wherein 1-phenoxy-3-[2-(1,3,5-trimethylpyrimidin-2,4-dion-6yl-N-methylamino)-ethylamino]-propan-2-ol is administered.

6. The method of claim 1 wherein 1-phenoxy-3-[2-(1-allyl-3,5-dimethyl-pyrazol-4-ylamino)-ethylamino]-propan-2-ol is administered.

7. The method of claim 1 wherein 1-phenoxy-3[2-(1-n-propyl-3,5-dimethylpyrazol-4-ylamino)-ethylamino]-propan-2-ol is administered.

8. The method of claim 1 wherein 1-(4-hydroxyphenoxy)-3-[2-(1,3,5-trimethylpyrazol-4-ylamino)-ethylamino]-propan-2-ol is administered.

9. The method of claim 1 wherein 1-phenoxy-3-[2-(1,4-dimethylpyrazol-5-ylamino)-ethylamino]-propan-2-ol is administered.

10. The method of claim 1 wherein 0.1 to 50 mg per kg body weight per day are administered.

11. The method of claim 1 wherein 0.5 to 40 mg per kg body weight per day are administered.

* * * * *